United States Patent
Rich

(10) Patent No.: US 7,115,408 B1
(45) Date of Patent: Oct. 3, 2006

(54) METHOD OF STABILIZING HYALURONIDASE WITH ANNEXIN II

(75) Inventor: Kathryn A. Rich, South Pasadena, CA (US)

(73) Assignee: ISTA Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 10/139,139

(22) Filed: May 2, 2002

Related U.S. Application Data

(60) Provisional application No. 60/288,162, filed on May 2, 2001.

(51) Int. Cl.
*C12N 9/26* (2006.01)
(52) U.S. Cl. ..................................................... 435/201
(58) Field of Classification Search ................ 435/201
See application file for complete search history.

(56) References Cited

U.S. PATENT DOCUMENTS 2,806,815 A * 9/1957 Singher et al. ............. 435/188
5,866,120 A    2/1999 Karageozian et al. ..... 424/94.62

OTHER PUBLICATIONS

Rich et al., "Accelerated clearance of experimental vitreous hemorrhage by Vitrase® : Relative roles of annexin II and hyaluronidase", IOVS 41 (4) : S361 (Mar. 15, 2000).*
Mochida et al. "Stability of purified hyaluronidase in aqueous solutions in the presence of several pssible protective agents", Yakugaku Zasshi 80: 1173-6 (1960).*

* cited by examiner

*Primary Examiner*—Sandra E. Saucier
(74) *Attorney, Agent, or Firm*—Knobbe, Martens, Olson & Bear, LLP

(57) ABSTRACT

This invention relates generally to the use of annexin II for the purpose of stabilizing a hyaluronidase enzyme for administration to the eyes of humans or other mammals.

2 Claims, 4 Drawing Sheets

METHOD OF STABILIZING HYALURONIDASE WITH ANNEXIN II

CROSS-REFERENCE TO RELATED APPLICATIONS

This is a non-provisional application, which claims priority to U.S. Provisional Application No. 60/228,162, filed May 2, 2001.

BACKGROUND OF THE INVENTION

Field of the Invention

This invention relates generally to the use of annexin II for the purpose of stabilizing a hyaluronidase enzyme for administration to the eyes of humans or other mammals.

Anatomy of the Human Eye

In human beings, the anatomy of the eye includes a "vitreous body" which occupies approximately four fifths of the cavity of the eyeball, behind the lens. The vitreous body is formed of gelatinous material, known as the vitreous humor. Typically, the vitreous humor of a normal human eye contains approximately 99% water along with 1% macromolecules including: collagen, hyaluronic acid, soluble glycoproteins, sugars and other low molecular weight metabolites.

The retina is essentially a layer of nervous tissue formed on the inner posterior surface of the eyeball. The retina is surrounded by a layer of cells known as the choroid layer. The retina may be divided into a) an optic portion which participates in the visual mechanism and b) a non-optic portion which does not participate in the visual mechanism. The optic portion of the retina contains the rods and cones, which are the effectual organs of vision. A number of arteries and veins enter the retina at its center, and splay outwardly to provide blood circulation to the retina. The posterior portion of the vitreous body is in direct contact with the retina.

The Causes, Treatments and Clinical Sequelae of Intra-Vitreal Hemorrhage

Diabetic retinopathy, trauma and other ophthalmological disorders sometimes result in the rupture or leakage of retinal blood vessels with resultant bleeding into the vitreous humor of the eye (ie., intravitreal hemorrhage). Such intravitreal hemorrhage typically manifests as clouding or opacification of the vitreous humor.

The presence of hemorrhagic blood within the vitreous body causes multiple clinical problems. These problems include: the inability to visually examine and diagnose the site of the hemorrhage and/or any accompanying tear or detachment of the retina; impairment of the performance of transvitreal surgical procedures; and impairment of vision in the affected eye. Each of these problems is discussed below.

Intravitreal hemorrhage is often accompanied by tearing or detachment of the retina. In cases where the intravitreal hemorrhage is accompanied by such retinal trauma, it is important that the retinal tear or detachment be promptly diagnosed and repaired. Failure to do so may allow retinal photoreceptor cells in the region of the retinal trauma to die. Death of the photoreceptor cells of the retina may result in loss of vision. Furthermore, allowing the retinal tear or detachment to remain unrepaired for an extended period of time may result in further intravitreal hemorrhage, or the formation of fibrous tissue at the site of the hemorrhage. The formation of such fibrous tissue may ultimately result in the formation of an undesirable fibrous attachment between the vitreous body and the retina.

Once a retinal tear or detachment has been diagnosed it must be treated to prevent further damage to the subject's sight. The typical surgical procedure used to repair retinal tear or detachment requires that a clinician be able to look through the vitreous humor and visualize the damaged region of the retina (i.e., perform transvitreal viewing of the retina). When an intravitreal hemorrhage has occurred, the presence of the hemorrhagic blood within the vitreous can cause the vitreous to become so occluded or cloudy that the clinician is prevented from visualizing the retina through the vitreous. Such hemorrhagic clouding of the vitreous can take ~12 months or longer to clear sufficiently to permit transvitreal viewing of the retina. However, in view of the potential complications that may result from delayed diagnosis or treatment of a retinal tear or detachment, it is generally not desirable to wait for such natural clearance of the hemorrhagic blood to occur.

Diagnosis of a retinal tear or detachment is often difficult or impossible in the presence of an intravitreal hemorrhage. Even when the intravitreal hemorrhage is not accompanied by retinal tear or detachment, the occurrence of vitreal hemorrhagic clouding can prevent the clinician from performing routine funduscopic examination of the retina. Accordingly, elimination of an intravitreal hemorrhage can be extremely important for the health of a subject's retina.

Moreover, the presence of hemorrhagic blood within the vitreous can effect a subject's vision. The presence of hemorrhagic blood within the vitreous may significantly impair the patient's vision through the affected eye. These negative ramifications of vitreal hemorrhage persist until such time as the hemorrhagic blood has been substantially or fully cleared from the vitreous.

In cases where intravitreal hemorrhage has resulted in substantial clouding or opacification of the vitreous, the treating physician may have the option to perform a procedure known as a vitrectomy. During a vitrectomy, all or a portion of the vitreous body is removed from the interior of the eye and replaced with a clear liquid. A vitrectomy is performed to allow the clinician to visualize the retina sufficiently to proceed with the necessary retinal examination and/or surgical repair of the hemorrhage and any accompanying retinal tear or detachment.

Vitrectomy procedures are highly invasive, are skill-intensive, and are associated with several significant drawbacks, risks, and complications. Among these drawbacks, risks and complications are the potential that the act of removing the vitreous will cause further detachment or tearing of the retina. Additionally, removal of the vitreous may cause further hemorrhage from the already-weakened retinal blood vessels.

Ophthalmic Applications of Enzymes for Accelerating Hemorrhage Clearance

U.S. Pat. No. 5,866,120 discloses a method for accelerating clearance of hemorrhagic blood from the vitreous humor of the eye. The disclosed method comprises the step of contacting a vitreous humor with an amount of an enzyme effective to cause accelerated clearance of blood therefrom. Specific enzymes disclosed in U.S. Pat. No. 5,866,120, as having a clearing effect included glycosaminoglycanases such as hyaluronidase, keratinase, chondroitinase AC, chondroitinase B and chondroitinase ABC; chondroitin sulfatases such as chondroitin 4 sulfatase chondroitin 6 sulfatase; matrix metalloproteinases such as matrix metalloproteinase- 1, matrix metalloproteinase-2, matrix metalloproteinase-3 and matrix metalloproteinase-9; and protein-kinases such as streptokinase and urokinase.

In particular, the patent discloses an improved, thimerosal-free, hyaluronidase preparation that is suitable for administration to the eye as a therapeutic agent. This hyaluronidase preparation comprises a preferred hyaluronidase enzyme that is substantially devoid of hyaluronidase molecules having molecular weights in excess of 100,000, between 60,000–70,000 and/or below 40,000. The hyaluronidase enzyme may be obtained from ovine testes and may be combined in aqueous solution with quantities of lactose and phosphate, to provide a thimerosal-free aqueous hyaluronidase solution for intraocular administration. This new hyaluronidase preparation could be administered to the eye at dosage levels sufficient to bring about optimal therapeutic effects, but does not cause toxicity.

Vitreous hemorrhages are notoriously slow to clear, sometimes taking many months. Studies have shown that the body's natural response to blood in the vitreous is very sluggish. Infiltration of inflammatory cells into injured tissue in response to chemotactic signals is a hallmark of wound repair. Polymorphonuclear leucocytes (PMNs) are generally the first cells that migrate into tissues in response to insults. By the third day, the number of PMNs begins to decease and other cell types, such as mononuclear phagocytes, begin to appear. The infiltrated inflammatory cells release a number of different cytokines and proteases, which then orchestrate the complex network of cellular interactions during wound healing and blood clearance.

Unlike hemorrhages in other tissues, in the vitreous there is almost no PMN response. Macrophage-type cells are seen in the area of the clot, but their ability to clear away the fibrin and red blood cells appears very slow and inefficient. (Spraul and Grossniklaus, Surv Ophthalmol 42: 3–39, 1997). The reasons for this limited cellular response are not known, but it is possible the nature and composition of the vitreous results in inadequate chemotactic signals and/or a barrier to ingress of cells into the vitreous (LaNauze et al., Exp Eye Res 34:803–813, 1982).

Accordingly, there exists a need in the art for the elucidation and development of new methods and procedures for accelerating the clearance of hemorrhagic blood from the vitreous body of the eye so as to permit trans-retinal viewing of the posterior aspect of the eye, including the retina.

SUMMARY OF THE INVENTION

In this invention it is surprisingly found that annexin II has unexpected good capacities as a liquid enzyme stabilizer.

DETAILED DESCRIPTION OF THE PREFERRED EMBODIMENT

Figure 1:
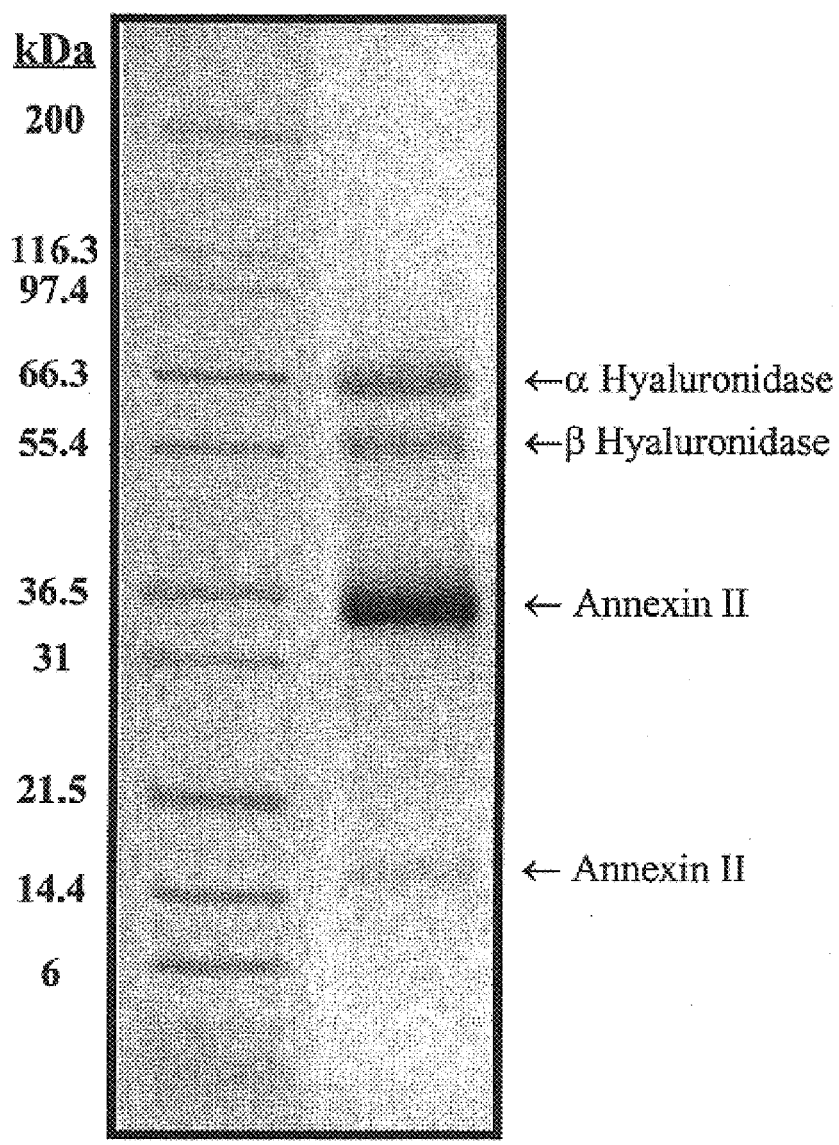
FIG. 1 shows an SDS-PAGE electrophoresis gel having in lane 1: molecular weight standards from 6000 through 200,000 kDa, and in lane 2: hyaluronidase (ACS)/Vitrase™ (hyaluronidase preparation).

The present invention arises from the unexpected discovery of the ability of annexin II to stabilize a liquid enzyme.

Annexins are a group of calcium-dependent, phospholipid-binding proteins. The annexins were first described as a family of proteins in 1990 (Crumpton and Dedman, Nature 345: 212, 1990), but had previously been isolated and characterized under a variety of different names. To date, over 20 members of the annexin family have been identified, 10 of which have been described in mammals. Their structure is characterized by repetitive homologous domains consisting of sequences of about 70 amino acids, with most annexins having four of these domains. The knowledge of the function(s) of the annexins is still limited, although these proteins are known to be widely distributed throughout the body, and they have been implicated in an array of physiological processes such as cell differentiation, mitogenesis, exocytosis, and endocytosis (Raynal and Pollard, Biochim Biophys Acta 1197: 63–93, 1994). The annexins are primarily cytosolic, but have been found on the surfaces of leucocytic and endothelial cells. In addition, soluble annexins are present in blood plasma and in bodily secretions.

Annexin II (p36) is unique among the annexins in that the predominant form in most cells is a heterotetrameric complex, whereas all other annexins exist as monomeric proteins. Studies conducted at ISTA Pharmaceuticals indicate that Annexin II isolated from ovine testes contains the monomeric protein rather than the heterotetrameric complex. The N-terminus of annexin II contains a high affinity binding site for a dimeric protein (p11) which is a member of the S100 family of $Ca^{++}$-binding proteins. The heterotetrameric complex formed by these proteins is referred to as annexin II tetramer. (AIIt; Waisman, Mol Cell Biochem 149/150: 301–322, 1995). Annexin II tetramer was initially shown to be present at the cytosolic surface of the plasma membrane of many cells. More recently, annexin II tetramer has been shown to exist on the extracellular surface of the plasma membrane of endothelial cells, macrophages, and certain tumor cells. (Balch and Dedman, Exp Cell Res, 237: 259–263, 1997; Siever and Erickson, Int J Biochem Cell Biol 29: 1219–1223, 1997).

Annexin II employed in the invention method can be obtained from any species, preferably mammals. It can be obtained through protein purification of tissue preparations or manufactured by expression of recombinant annexin II genes. These techniques are well known in the art. For example, Moore KG, et al., "Purification of annexin I and annexin II from human placental membranes by high-performance liquid chromatography," Protein Expr Purif. 1992 February;3(1):1–7, discusses the purification of annexin II. Annexin II is also available commercially from BioDesign, Int. (Kennebunk, Me.).

According to the invention the liquid composition may contain up to 500 mM of the stabilizer, preferably the liquid composition may contain 0.001–250 mM of the stabilizer, more preferably the liquid composition may contain 0.005–100 mM of the stabilizer, most preferably the liquid composition may contain 0.01–10 mM of the stabilizer.

According to the invention the liquid composition contains at least one enzyme. The enzyme may be any commercially available enzyme, in particular an enzyme selected from the group consisting of proteases, amylases, lipases, cellulases, peroxidases or glycosaminoglycanases or any mixture thereof. Mixtures of enzymes from the same class (e.g. lipases) are also included.

The amount of enzyme used in the composition varies according to the type of enzyme(s) and the use intended. If the liquid is a phosphate/lactose liquid, the amount of each enzyme will typically be 0.2–40 µM, especially 0.4–20 µM (generally 5–1000 mg/l, especially 10–500 mg/l) calculated as pure enzyme protein.

Protease: Any protease suitable for use in a liquid composition can be used. Suitable proteases include those of animal, vegetable or microbial origin. Chemically or genetically modified mutants are included.

Amylase: Any amylase suitable for use in a liquid composition can be used. Suitable amylases include those of bacterial and fungal origin. Chemically or genetically modified mutants are included.

Lipase: Any lipase suitable for use in a liquid composition can be used. Suitable lipases include those of bacterial and fungal origin. Chemically or genetically modified mutants are included.

Cellulase: Any cellulase suitable for use in a liquid composition can be used. Suitable cellulases include those of bacterial and fungal origin. Chemically or genetically modified mutants are included.

Peroxidase: Any peroxidase suitable for use in a liquid composition can be used herein. Suitable peroxidases herein include those of plant, bacterial and fungal origin. Chemically or genetically modified mutants are included.

Glycosaminoglycanase: Any glycosaminoglycanase suitable for use in a liquid composition can be used. Suitable glycosaminoglycanases include those of animal or microbial origin. Chemically or genetically modified mutants are included. Preferred is hyaluronidase, keratinase, chondroitinase AC, chondroitinase B chondroitinase ABC, chondroitin 4 sulfatase and chondroitin 6 sulfatase Particularly preferred is hyaluronidase.

A general formulation for an injectable annexin II stabilized hyaluronidase preparation, of the present invention is shown in Table I as follows:

TABLE I

General Formulation

| Ingredient | Quantity |
| --- | --- |
| Hyaluronidase ACS | 1.0 IU–8000 IU |
| Annexin II | up to 20 ug |
| Lactose, USP/sorbitol | 13.3 mg–130.0 mg |
| Phosphate, USP | 5–200 mmoles |

These formulation ingredients are initially dissolved in sterile water, sterile filtered and subsequently dispensed as a solution into glass vials or glass syringes. In addition the solution could be lyophilized to a dry composition. The lyophilized composition is packaged for subsequent reconstitution prior to use, in balanced salt solution or sterile isotonic saline solution. Such balanced salt solution typically contains: 0.64% sodium chloride, 0.075% potassium chloride, 0.048% calcium chloride dihydrate, 0.03% sodium acetate trihydrate, 0.17% sodium citrate dihydrate, sodium hydroxide/hydrochloric acid to adjust the pH, and water for injection to 100%.

FIG. 1 shows an electrophoresis gel (4–20% gradient SDS-PAGE under non-reducing conditions) which demonstrates the molecular weight distribution of the proteins in hyaluronidase (ACS)/Vitrase™ (hyaluronidase preparation) after staining with Coomassie Blue. Lane 1 contains molecular weight markers at 200,000; 116,300; 97,400; 66,300; 55,400; 36,500; 31,00; 21,500; 14,400 and 6000 kDa. Lane 2 contains 75 IU of hyaluronidase (ACS)/Vitrase™ (hyaluronidase preparation), lot 222B. Protein bands can be seen at 68 kDa; 58 kDa; 36 kDa and at 14 kDa. Some other lots of hyaluronidase (ACS)/Vitrase™ (hyaluronidase preparation) also have a protein band at 24 kDa.

Zymogram for hyaluronic acid lysing activity: Various lots of hyaluronidase (ACS)/Vitrase™ (hyaluronidase preparation), (60 mU/lane) were subjected to 10% gel SDS-PAGE containing 1 mg/ml hyaluronic acid. Gels were incubated in 2.5% Triton-X 100 for 1 hr at room temperature to allow for protein renaturation. This was followed by an overnight incubation at 37° C. in 50 mM Tris buffer, pH 7.4 (containing NaCl, $CaCl_2$ and Brij-35) to allow for hyaluronan digestion. The gel was stained with 0.05% Alcian Blue to visualize areas of hyaluronidase activity.

Figure 2:
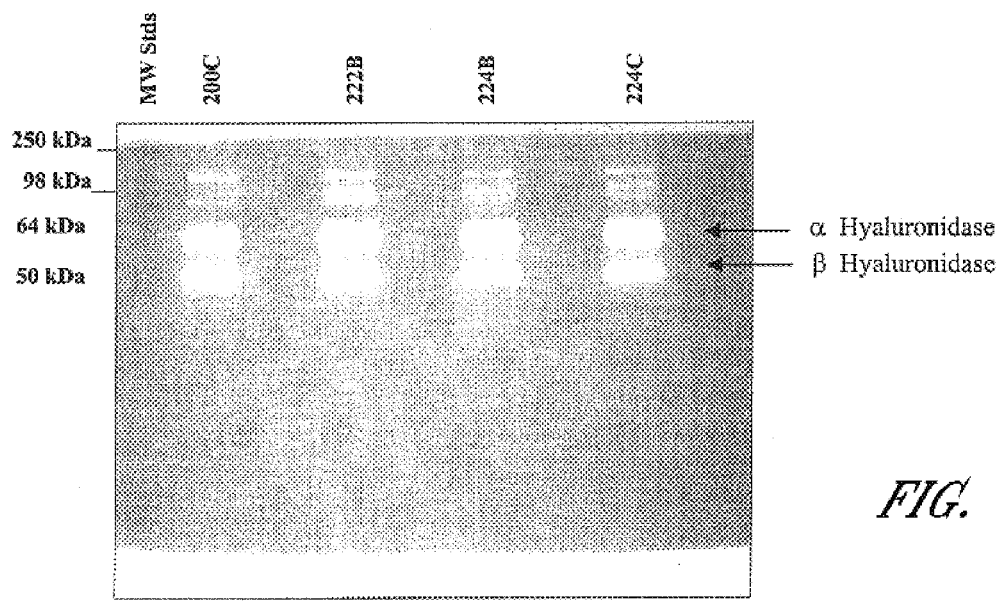
FIG. 2 shows a zymogram determining hyaluronic acid lysing activity of hyaluronidase (ACS)/Vitrase™ (hyaluronidase preparation).

By use of hyaluronan zymography (FIG. 2), it can be shown that both the 58 kDa and the 68 kDa species possess hyaluronidase activity. These two species have been designated as α and β hyaluronidase. The α-form is believed to be a membrane-associated form, while the β-form is likely to be a processed soluble form of hyaluronidase.

Figure 3:
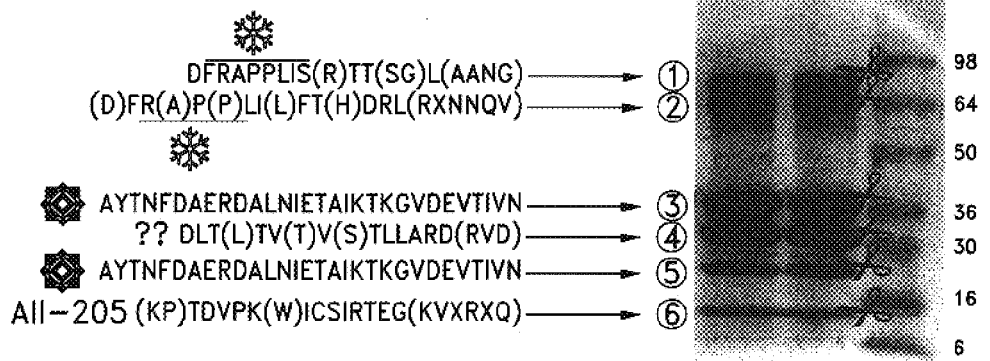
FIG. 3 shows an electrophoresis gel of hyaluronidase (ACS)/Vitrase™ (hyaluronidase preparation) and identification of hyaluronidase and annexin II sequences in the preparation as determined by N-terminal sequencing of individual protein bands.

In order to identify the additional protein components in hyaluronidase (ACS)/Vitrase™ (hyaluronidase preparation) raw material, the proteins were subjected to SDS-PAGE (under reducing conditions) and the N-terminal sequences of 6 individual protein bands were analyzed (FIG. 3).

N-terminal sequencing: Hyaluronidase (ACS)/Vitrase™ (hyaluronidase preparation) (120 IU) was subjected to 4–20% gradient gel SDS-PAGE under reducing conditions. The proteins were then electrophoretically transferred to a PVDF membrane. The protein bands were identified by Coomassie Blue staining. Individual bands of interest were isolated by excision. Four protein bands were submitted for automated Edman degradation at the UCLA Protein Sequencing Core Facility.

The amino acid sequences of the two high molecular weight components showed homology to known sequences for hyaluronidases, as expected. The N-terminal sequence for the protein band at around 36 kDa showed homology to the published sequence for heavy chain of annexin II, as did two of the lower molecular weight bands (24 and 14 kDa). The amino acid sequence of the protein band at around 32 kDa did not match with any published sequence.

Figure 4:
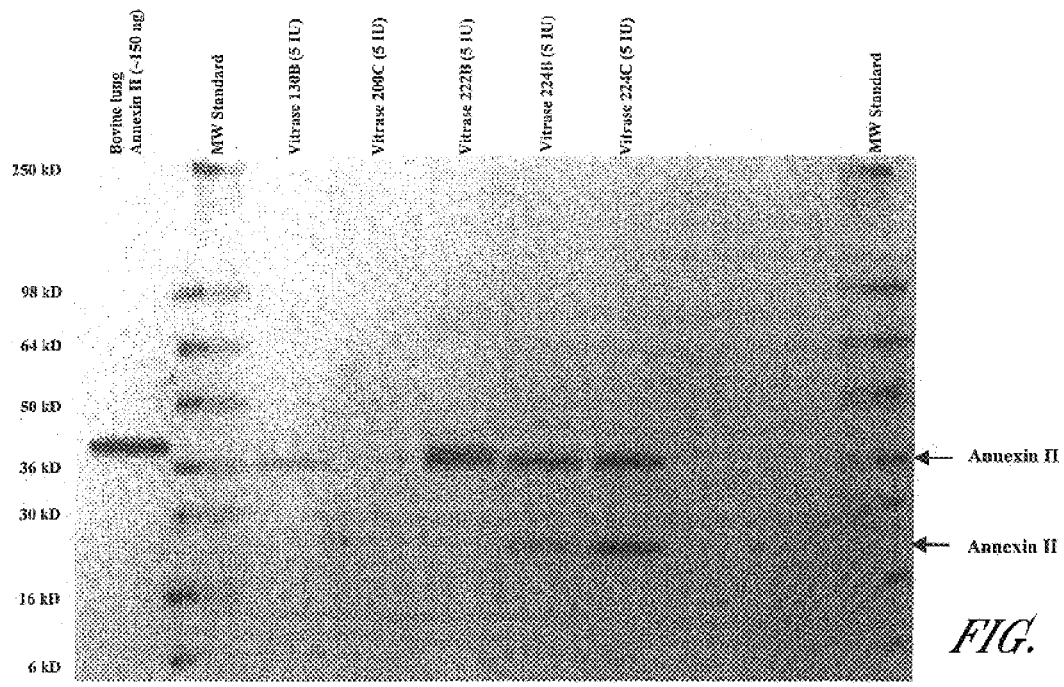
FIG. 4 is a Western blot of hyaluronidase (ACS)/Vitrase™ (hyaluronidase preparation) preparations developed with a monoclonal antibody to annexin II.

The identity of annexin II as a component of hyaluronidase (ACS)/Vitrase™ (hyaluronidase preparation) preparations was further confirmed by Western blotting with a monoclonal antibody to annexin II (FIG. 4).

Western blotting: Various lots of hyaluronidase (ACS)/Vitrase™ (hyaluronidase preparation) (5 IU/lane) were subjected to 4–20% gradient gel SDS-PAGE along with a purified preparation of annexin II from bovine lung (~150 ng; BioDesign, Int. (Kennebunk, Me.)). The proteins were electrophoretically transferred to a nitrocellulose membrane, blocked with BSA and then incubated with a monoclonal antibody to annexin II (1:500; Transduction Laboratories). After incubation with biotinylated anti-mouse IgG, the reactive bands were visualized with an avidin-conjugated HRP/DAB system (Vector Laboratories).

The preferred injectable solution of annexin II stabilized hyaluronidase may contain, in addition to annexin II, certain inactive ingredients which cause the solution to be substantially isotonic, and of a pH which is suitable for injection into the eye. Such solution of stabilized hyaluronidase for injection may be in glass vials or pre-filled syringes maintained at room temperature or refrigerated temperature, ready for use. In addition such solutions of stabilized hyaluronidase may be initially lyophilized to a dry state and thereafter, may be reconstituted prior to use.

More specifically, the annexin II stabilized hyaluronidase may be prepared in accordance with the specific formulation shown in Table II here below.

TABLE II

Specific Formulation

| Ingredient | Quantity |
| --- | --- |
| Hyaluronidase | 1.0 IU–8000 IU |
| Annexin II | .01–20 µg |
| Lactose USP/Sorbitol | 13.3 mg–150 mg |
| Phosphate USP | 5 mmoles–50 mmoles |
| Sodium Chloride USP | Make isotonic |

The specific preferred formulation of annexin II stabilized hyaluronidase set forth in Table II may be injected directly into the vitreous of the eye at dosage levels which bring about desirable therapeutic effects, including but not necessarily limited to the intravitreal hemorrhage clearing effect, without causing significant toxicity to the eye or associated anatomical structures.

The preferred route of administration is by intra-vitreal injection, whereby an injectable solution containing annexin II stabilized hyaluronidase is injected, through a needle, directly into the vitreous body located within the posterior chamber of the eye. Alternatively, however, a hemorrhage-clearing amount of annex in II stabilized hyaluronidase can be administered by any other suitable route of administration (e.g., topically, by contact lens, etc.) which results in sufficient distribution of the compound(s) to the vitreous body to cause the desired hemorrhage-clearing effect.

EXAMPLES

Example I

Room Temperature Stability of Hyaluronidase Enzyme in the Presence of Annexin II Three separate batches of hyaluronidase enzyme solutions were prepared containing the following ingredients:

| 1. Hyaluronidase Solution Peak II | |
| --- | --- |
| Ovine Hyaluronidase | 1800 IU/ml. |
| Lactose, N.F. | 1.25 mg/ml. |
| Potassium Phosphate Monobasic, N.F. | 0.305 mg/ml. |
| Potassium Phosphate Dibasic, U.S.P. | 0.48 mg/ml. |
| Sodium Chloride, U.S.P. | 9.0 mg/ml. |
| Packaged in a 3.0 ml glass vial. | |

The hyaluronidase enzyme in this formulation is almost free of Annexin II.

| 2. Hyaluronidase Solution ACS 001-3 (Lot 222B). | |
| --- | --- |
| Ovine Hyaluronidase | 1500 IU/ml. |
| Lactose, N.F. | 1.25 mg/ml. |
| Potassium Phosphate Monobasic, N.F. | 0.305 mg/ml. |
| Potassium Phosphate Dibasic, U.S.P. | 0.48 mg/ml. |
| Sodium Chloride, U.S.P. | 9.0 mg/ml. |
| Packaged in a 3.0 ml glass vial. | |

The hyaluronidase enzyme in this formulation has annexin II.

| 3. Hyaluronidase Solution PHI-12-15 (Lot 222B) | |
| --- | --- |
| Ovine Hyaluronidase | 1500 IU/ml. |
| Lactose, N.F. | 1.25 mg/ml. |
| Potassium Phosphate Monobasic, N.F. | 0.305 mg/ml. |
| Potassium Phosphate Dibasic, U.S.P. | 0.48 mg/ml. |
| Sodium Chloride, U.S.P. | 9.0 mg/ml. |
| Packaged in a 1.0 ml glass syringe. | |

The hyaluronidase enzyme in this formulation has annexin II.

The three hyaluronidase enzyme solutions were placed in controlled room temperature conditions. At pre-determined time points, samples were taken and analyzed for hyaluronidase enzyme activity. The results are summarized in Table III, below.

TABLE III

25° C. Stability Hyaluronidase Solutions

| WEEKS/ MONTHS | Hyaluronidase Solution Peak II | Hyaluronidase Solution ACS 001-3 (Lot 222B) | Hyaluronidase Solution PHI-12-15 (Lot 222B) |
| --- | --- | --- | --- |
| Zero Time | 100% Activity | 100% Activity | 100% Activity |
| 2 Weeks | 78% Activity | — | — |
| 1 Month | 79% Activity | 107% Activity | 112% Activity |
| 2 Month | Results unavailable | 104% Activity | 110% Activity |
| 3 Month | — | 98% Activity | 102% Activity |
| 6 Month | — | 96% Activity | 95% Activity |
| 9 Month | — | 95% Activity | 79% Activity |
| 12 Month | — | 72% Activity | 63% Activity |

The results of this stability study for the three hyaluronidase solutions include the following observations:

a) Hyaluronidase Solution Peak II that contains barely detectable levels of Annexin II is unstable. This solution looses 21% of hyaluronidase activity within 1 month of room temperature storage.

b) In comparison hyaluronidase solution ACS 001-3 takes 12 months to loose 28% of enzyme activity. Furthermore hyaluronidase solution PHI-12-15 takes 9 months to loose 21% of enzyme activity.

c) The results show a dramatic improvement of hyaluronidase enzyme stability at room temperature when the enzyme is together with annexin II.

Having now fully described the invention, it will be understood by those of ordinary skill in the art, that the same can be performed within a wide equivalent variation of conditions, formulations and other parameters, without affecting the scope of the invention or any embodiment therein. All publications cited herein are fully incorporated by reference herein in their entirety.

What is claimed is:

1. A method of stabilizing a liquid composition comprising:
   (a) identifying a liquid enzyme in need of stabilization, and
   (b) adding annexin II to said liquid enzyme in need of stabilization, wherein said liquid enzyme is hyaluronidase.

2. A method of stabilizing a liquid composition comprising:
   (a) adding annexin II to a liquid enzyme in need of stabilization, wherein said liquid enzyme is hyaluronidase, and
   (b) measuring stabilization of said liquid enzyme.

* * * * *